US008207121B2

(12) United States Patent
Brown et al.

(10) Patent No.: US 8,207,121 B2
(45) Date of Patent: Jun. 26, 2012

(54) SENSITIZATION TO ANOTHER ANTICANCER THERAPY AND/OR AMELIORATION OF A SIDE EFFECT OF ANOTHER ANTICANCER THERAPY BY TREATMENT WITH A GST-ACTIVATED ANTICANCER COMPOUND

(75) Inventors: Gail L. Brown, Woodside, CA (US); James G. Keck, Redwood City, CA (US); Michael M. Wick, Woodside, CA (US)

(73) Assignee: Telik, Inc., Palo Alto, CA (US)

( * ) Notice: Subject to any disclaimer, the term of this patent is extended or adjusted under 35 U.S.C. 154(b) by 760 days.

(21) Appl. No.: 11/872,662

(22) Filed: Oct. 15, 2007

(65) Prior Publication Data

US 2008/0166428 A1    Jul. 10, 2008

Related U.S. Application Data

(63) Continuation of application No. 11/133,833, filed on May 19, 2005, now abandoned.

(60) Provisional application No. 60/572,790, filed on May 20, 2004.

(51) Int. Cl.
*A61P 35/00* (2006.01)
*G01N 33/574* (2006.01)
*C12N 5/09* (2010.01)

(52) U.S. Cl. ......... 514/19.3; 435/7.23; 435/344; 436/64

(58) Field of Classification Search .................. None
See application file for complete search history.

(56) References Cited

U.S. PATENT DOCUMENTS

| 5,556,942 | A | 9/1996 | Kauvar et al. |
| 5,767,147 | A | 6/1998 | Jones et al. |
| 5,880,097 | A | 3/1999 | Lyttle et al. |
| 6,281,223 | B1 | 8/2001 | Choy et al. |
| 2004/0138140 | A1 | 7/2004 | Xu et al. |

FOREIGN PATENT DOCUMENTS

| WO | WO 95/09865 | 4/1995 |
| WO | WO 96/40205 | 12/1996 |
| WO | WO 2004/045593 | 6/2004 |
| WO | WO 2005/112973 | 12/2005 |

OTHER PUBLICATIONS

Keck, et al., Eur. J. Cancer, 2002, 38 (Suppl. 7), Abs 102.*
DeGuzman, Telik News Release, Dec. 9, 2002, 2 pages.*
Morgan AS et al., "Tumor Efficacy and Bone Marrow-sparing Properties of TER286, a Cytotoxin Activated by Glutathione S-Transferase", *Cancer Res.*, v. 58, pp. 2568-2575, Jun. 15, 1998.
Kauvar LM et al., "Glutathione Based Approaches to Improving Cancer Treatment", *Chemico-Biological Interactions*, v. 111-112, pp. 225-238, 1998.
Rosario LA, et al., "Cellular Response to a Glutathione S-Transferase P1-1 Activated Prodrug", *Mol. Pharmacol.*, v. 58, pp. 167-174, 2000.
Telik press release, "Telik Announces Initiation of TLK286 Combination Chemotherapy Development Program", 2 pgs., Oct. 7, 2002.
Anonymous: "Two secondary offerings hopeful?", SCRIP, No. 2790, p. 12, Oct. 16, 2002.
Telik press release, "Telik Presents Preclinical Data Demonstrating Synergy of TLK286 in Combination with Multiple Approved Cancer Chemotherapy Drugs", 2 pgs., Nov. 20, 2002.
Poster (Keck JG et al.) shown at the 14th EORTC-NCI-AACR Symposium, 1 pg., Nov. 20, 2002.
Telik press release, "Telik Announces Initiation of Two Additional Clinical Trials of TLK286 in Combination Chemotherapy Regimes", 2 pgs., Dec. 9, 2002.
Abstract #1722 for 94th Annual Meeting of AACR, in *Proc. Am. Assn. Cancer Res.*, v. 44, 4 pgs., Mar. 10, 2003, (date of posting on AACR Website).
Telik press release, "Telik Announces New Preclinical Data on TLK286 That Supports Unique Mechanism of Activation, and Activity in Combinations With Standard Cancer Drugs", 2 pgs., Apr. 9, 2003 Note that this press release is not correct in describing Abstract #LB123—no such abstract was published the Mar. 2003 *Proc. Am. Assn. Cancer Res.*
Telik press release, "Telik Announces Positive Interim Results from Phase 1-2a Trial of Telcyta™ (TLK286) in Combination with Doxil®", 2 pgs., Oct. 21, 2003.
Telik press release, "Telik Announces Positive Interim Results from Phase 1-2a Trial of Telcyta™ (TLK286) in Combination with Docetaxel" 2 pgs., Oct. 21, 2003.
Telik press release, "Telik Announces Positive Interim Results from Phase 1-2a Trial of Telcyta™ (TLK286) in Combination with Carboplatin" 2 pgs., Oct. 21, 2003.
Telik press release, "Telik Announces Presentations at AACR-NCI-EORTC Conference", 2 pgs., Nov. 13, 2003.
Abstracts #C139, #C153, #C155, #C156 for 2003 AACR-NCI-EORTC International Conference, 4 pgs., Nov. 17, 2003 Note: Also published in *Clin. Cancer Res.*, v. 9, No. 16, Dec. 1, 2003.
Telik press release, "Telik's Telcyta™ Demonstrates 63% Objective Response Rate in Combination with Carboplatin in Platinum Refractory or Resistant Ovarian Cancer in a Phase 1-2a Trial", 3 pgs., Nov. 19, 2003.
Telik press release, "Telik Announces Interim Results Showing Clinical Efficacy with Telcyta™ in Combination with Docetaxel in Phase 1-2a Clinical Trial in Second and Third Line Non-Small Cell Lung Cancer Patients", 3 pgs., Nov. 19, 2003.
Telik press release, Telik Announces Positive Interim Results from Phase 1-2a Clinical Trial of Telcyta™ in Combination with Doxil® in Platinum Refractory or Resistant Ovarian Cancer, 3 pgs., Nov. 19, 2003.

(Continued)

*Primary Examiner* — Cecilia J Tsang
*Assistant Examiner* — Satyanarayana R Gudibande
(74) *Attorney, Agent, or Firm* — Foley & Lardner LLP

(57) ABSTRACT

A method of sensitizing a mammal, especially a human, to another anticancer therapy by administering a sensitizing effective amount of a GST-activated anticancer compound. A method of ameliorating a side effect of another anticancer therapy in a mammal, especially a human, by administering an ameliorating effective amount of a GST-activated anticancer compound. Pharmaceutical compositions for the methods. The GST-activated anticancer compound is preferably a compound of U.S. Pat. No. 5,556,942, and more preferably canfosfamide, especially as the hydrochloride salt.

2 Claims, No Drawings

OTHER PUBLICATIONS

Poster (Kavanagh JJ et al.) shown at the 2003 AACR-NCI-EORTC International Conference, 1 pg., Nov. 20, 2003.
Poster (Papadimitrakopoulou V et al.) shown at the 2003 AACR-NCI-EORTC International Conference, 1 pg., Nov. 20, 2003.
Poster (Xu H et al.) shown at the 2003 AACR-NCI-EORTC International Conference, 1 pg., Nov. 20, 2003.
Abstract #238 for 35th Annual Meeting of the Society of Gynecologic Oncologists (SGO), 3 pgs., Feb. 7-11, 2004.
Poster (Kavanagh JJ et al.) shown at the 35th Annual Meeting of SGO, Feb. 10, 2004.
Kavanagh JJ et al, "Phase 2 Study of TLK286 (Telcytatm, A GST P1-1 Activated Glutathione Analog) in Patients With Platinum and Paclitaxel Refractory or Resistant Ovarian Cancer" *Proceedings From the 2004 Annual Meeting of the Society of Gynecologic Oncologists*, pp. 1-3, XP002345165, CME article at http://professional.cancerconsultants.com/jc_issue2_ovarian.aspx?id=30360, accessed Sep. 13, 2005.
Abstracts #559 and #2008 for 95th Annual Meeting of AACR, from *Proc. Am. Assn. Cancer Res.*, v. 45, 3 pgs., Mar. 2004 (probably made available online in late Feb. 2004, certainly available by Mar. 27, 2004—first day of the meeting).
Telik press release, "Telik Initiates Telcyta™ Trial in Front-Line Treatment of Non-Small Cell Lung Cancer"; 2 pgs, Mar. 9, 2004.
Abstract, Database Pharmaprojects Online, PJB Publications Ltd, United Kingdom, Database accession No. 10581, 3 pgs, (reportedly updated on Mar. 12, 2004—see p. 3, line 3).
Telik press release, "Telik Announces Telcyta™ Presentations and American Association for Cancer Research Annual Meeting", 2 pgs., Mar. 25, 2004.
Poster (Xu H et al.) shown at the 2004 95th Annual Meeting of AACR, Mar. 28, 2004.
Telik press release, "Telik Reports Positive Telcyta™ Data Supporting Use in Combination Chemotherapy Regimens", 2 pgs, Mar. 30, 2004.
Rosen LS et al, "Phase 1 Study of TLK286 (Telcyta) Administered Weekly in Advanced Malignancies" *Clin. Cancer Res.*, v. 10 (11), pp. 3689-3698 (Jun. 1, 2004).
Abstracts #5060, #5062, #7140 for 40th Annual Meeting of the American Society for Clinical Oncology (ASCO), 4 pgs, Jun. 5-8, 2004. Note: The Annual Meeting Proceedings Abstracts were mailed to members on approximately May 18, 2004, but were embargoed and confidential, and were not publicly released until Jun. 5, 2004.
Telik press release, "Telik Announces 56% Objective Response Rate of Telcyta™ in Combination with Carboplatin in Phase 2 Study in Platinum Refractory or Resistant Ovarian Cancer", 3 pgs., Jun. 5, 2004.
Telik press release, "Telik Announces 46% Objective Response Rate in Phase 2 Trial of Telcyta™ in Combination with Liposomal Doxorubicin in Platinum Refractory or Resistant Ovarian Cancer", 2 pgs., Jun. 5, 2004.
Telik press release, "Telik Announces 27% Objective Response Rate in Phase 2 Trial of Telcyta™ in Combination with Docetaxel in Platinum-Resistant Non-Small Cell Lung Cancer", 2 pgs., Jun. 5, 2004.
Poster (Kavanagh JJ et al.) shown at the 40th Annual Meeting of ASCO, Jun. 5, 2004.
Poster (Papadimitrakopoulou V et al.) shown at the 40th Annual Meeting of ASCO, Jun. 5, 2004.
Telik press release, "Telik Initiates First Triplet Combination Trial with Telcyta in Front-Line Treatment of Non-Small Cell Lung Cancer", 2 pgs., Jun. 30, 2004.
Abstract #095 for 10th Biennial Meeting of the International Gynecologic Cancer Society (IGCS) (Oct. 3-7, 2004), from *Int. J. Gyn. Cancer*, v. 14 (Suppl. 1), 3 pgs., Sep./Oct. 2004.
Telik press release, "Telik Announces Updated Positive Results From Phase 2 Trial of Telcyta in Combination with Carboplatin", 2 pgs, Oct. 4, 2004.
Telik press release, "Telik Announces Additional Positive Results From Phase 2 Trial of Telcyta in Combination with Doxil", 2 pgs, Oct. 4, 2004.
Poster (Kavanagh JJ et al.) shown at the 10th Biennial Meeting of IGCS, Oct. 4, 2004.
Telik press release, "Telik Completes Enrollment in ASSIST-1, Initiates ASSIST-3 and Reviews Status of ASSIST-2 Clinical Trials", 2 pgs, Dec. 29, 2004.
Abstracts #1500 and #4991 for 96th Annual Meeting of AACR, from *Proc. Am. Assn. Cancer Res.*, v. 46, 4 pgs., Apr. 2005, (available by Apr. 16, 2005—first day of the meeting).
Telik press release, "Telik Announces Presentations at American Association for Cancer Research Annual Meeting", 2 pgs, Apr. 13, 2005.
Poster (Wang Z et al.) shown at the 96th Annual Meeting of AACR, Apr. 17, 2005.
Poster (Xu H et al.) shown at the 96th Annual Meeting of AACR, Apr. 17, 2005.
Telik press release, "Telik Reports Telcyta Data at American Association for Cancer Research Annual Meeting", 2 pgs, Apr. 19, 2005.
Abstracts #7126 and 7275 for 41st Annual Meeting of ASCO, from *J. Clin. Oncol.*, v. 23 (16S), 3 pgs., Jun. 1, 2005 (available by May 13, 2005—first day of the meeting) Note: The Annual Meeting Proceedings Abstracts were mailed to members on approximately 2-3 weeks prior to the meeting, but were embargoed and confidential, and were not publicly released until May 13, 2005.
Poster (Burris et al.) shown at the 41st Annual Meeting of ASCO, May 17, 2005.
Telik press release, "Telik Reports Positive Interim Results of Telcyta in Combination with Cisplatin in First-Line Non-Small Cell Lung Cancer", 2 pgs, May 17, 2005.
USP Dictionary of USAN and International Drug Names (2005), 3 pgs, entry for canfosfamide.
Kavanagh JJ et al, "Multi-Institutional Phase 2 Study of TLK286 (Telcyta(TM), A Glutathione S-Transferase P1-1 Activated Glutathione Analog Prodrug) in Patients With Platinum and Paclitaxel Refractory or Resistant Ovarian Cancer", *Int. J. Gynecol. Cancer*, v. 15(4), pp. 593-600 (2005).
Tew KD; "TLK-286: A Novel Glutathione S-Transferase-Activated Prodrug"; *Expert Opin. Investig. Drugs*, v. 14(8), pp. 1047-1054 (2005).
Accession No. EMB-2005094524: abstract of Reed NS et al, "Role of Chemotherapy in the Management of Epithelial Ovarian Cancer"; *Exp. Rev. Anticancer Therapy*, v.5 (1), pp. 139-147 (2005).
Keck, et al. Eur. J. Cancer, 2002, 38 (Suppl. 7), Abs 102.
McIntyre, et al. Drugs of the Future, 2004, 29(10), 985-991.
DeGuzman, 2002, Telik News Release, pp. 1-2.
Papadimitrakopoulou, et al., 2002, Eur. J. Cancer, 38(7), Abstract 106A.
Xu et al. "Synergistic cancer cell cytotoxicity of TLK286 (Telcyta TM) in combination with carboplatin, cisplatin, doxorubicin, docetaxel, paclitaxel or oxaliplatin in human ovarian, lung, breast and colorectal cancer cell lines." Clinical Cancer Research, vol. 9, No. 16, Dec. 1, 2003, pp. 6241S-6242S, XP008053065.
"Enhanced antitumor activity of TLK286 in combination with carboplatin, doxorubicin and docetaxel in human ovarian and breast cancer cell lines." European Journal of Cancer, Pergamon Press, Oxford, GB, vol. 38, Nov. 2002, p. S35, XP004403542.

* cited by examiner

SENSITIZATION TO ANOTHER ANTICANCER THERAPY AND/OR AMELIORATION OF A SIDE EFFECT OF ANOTHER ANTICANCER THERAPY BY TREATMENT WITH A GST-ACTIVATED ANTICANCER COMPOUND

CROSS-REFERENCE TO RELATED APPLICATIONS

This application is a continuation and claims the benefit under 35 U.S.C. 120 of U.S. application Ser. No. 11/133,833, filed 19 May 2005, which in turn claims the benefit under 35 U.S.C. 119(e) of U.S. Provisional Application No. 60/572,790, filed 20 May 2004. The entire contents of both of these prior applications are incorporated into this application by reference.

SEQUENCE LISTING

The instant application contains a Sequence Listing which has been submitted in ASCII format via EFS-Web and is hereby incorporated by reference in its entirety. Said ASCII copy, created on Feb. 2, 2011, is named 056274-3515.txt and is 781 bytes in size.

BACKGROUND OF THE INVENTION

1. Field of the Invention
This invention relates to anticancer therapy.
2. Description of the Related Art
The purpose of anticancer therapy is to prevent cancer cells from multiplying, invading, metastasizing, and ultimately killing their host organism, e.g. a human or other mammal. Because cell multiplication is a characteristic of many normal cells as well as cancer cells, most anticancer therapies also have toxic effects on normal cells, particularly those with a rapid rate of turnover, such as bone marrow and mucous membrane cells. The goal in selecting an effective anticancer therapy, therefore, is to find a therapy that has a marked growth inhibitory or controlling effect on the cancer cells and a minimal toxic effect on the host. In the most effective therapies, the agents used are capable not only of inhibiting but also eradicating all cancer cells while sufficiently preserving normal cells to permit the host to return to normal or at least satisfactory life function and quality. Anticancer therapies include classic chemotherapy with antiproliferative agents (typically, small molecules) that target all dividing cells; molecular targeted therapy designed to specifically target cancer cells, such as functional therapy designed to alter a molecular function in the cancer cells with gene therapy, antisense therapy, and drugs such as erlotinib hydrochloride, gefitinib, and imatinib mesylate, and phenotype-directed therapy designed to target the unique phenotype of cancer cells such as therapy with monoclonal antibodies, immunotoxins, radioimmunoconjugates, and cancer vaccines; biologic therapy with cytokines such as interleukin-2 and interferon-α; and radiotherapy.

However, although the first effective anticancer compounds were brought into clinical trials in the 1940's, initial therapeutic results were disappointing. Regressions of acute lymphocytic leukemia and adult lymphomas were obtained with single agents such as the nitrogen mustards, antifolates, corticosteroids, and vinca alkaloids, but responses were frequently partial and only of short duration; and relapse was associated with resistance to the original drug. Initial resistance to a given single agent (natural resistance) is frequent, and even initially responsive cancers frequently display acquired resistance after drug exposure, probably owing to selection of pre-existing resistant cancer cells from a heterogeneous population and possibly also owing to an increased rate of mutation to resistance. This is consistent with the clinical observation that, with few exceptions, cancers are cured only by combination therapy. Cancers are frequently characterized as being resistant (not showing a response during the initial course of therapy) or refractory (having shown an initial response, then relapsed, and not showing a response on a later course of therapy) to anticancer therapies. Resistance to one anticancer drug, e.g. a platinum anticancer compound such as cisplatin, is often associated with cross-resistance to other drugs of the same class, e.g. other platinum compounds. Multiple drug resistance, also called pleiotropic drug resistance, is a phenomenon where treatment with one drug confers resistance not only to that drug and others of its class but also to unrelated agents.

Anticancer therapies, especially chemotherapies, are frequently employed in combination, for several principal reasons. First, treatment with two or more non-cross-resistant therapies may prevent the formation of resistant clones; second, the combination of two or more therapies that are active against cells in different phases of growth (resting—$G_0$, post-mitotic—$G_1$, DNA synthesis—S, premitotic—$G_2$, and mitotic—M) may kill cells that are dividing slowly as well as those that are dividing actively and/or recruit cells into a more actively dividing state, making them more sensitive to many anticancer therapies; and third, the combination may create a biochemical enhancement effect by affecting different pathways or different steps in a single biochemical pathway. Particularly when the toxicities of the therapies are non-overlapping, two or more therapies may be employed in full or nearly full amounts, and the effectiveness of each therapy will be maintained in the combination; thus, myelosuppressive drugs may be supplemented by non-myelosuppressive drugs such as the vinca alkaloids, prednisone, and bleomycin; and combination chemotherapies have been developed for a number of cancers that are not curable with single agents. Combinations of two or more of chemotherapy, molecular targeted therapy, biologic therapy, and radiotherapy are also known and used. Although the existence of a wide variety of mechanistically distinct anticancer therapies suggests that non-cross-resistant therapies can be found, cancer cells are known to possess a variety of mechanisms that confer pleiotropic drug resistance. These mechanisms of resistance contribute to the failure of combination therapy to cure common cancers such as metastatic colon cancer and prostate cancer.

A disadvantage of virtually all anticancer therapies is the occurrence of side effects, undesired effects caused by the anticancer therapy on a patient being treated for a cancer. While some effects are minor in their effect on the physical health of the patient, such as alopecia (which is common in patients treated with platinum compounds, taxanes, and anthracyclines), most others such as nausea, vomiting, and neutropenia (also common in patients treated with platinum compounds) can have such an effect on the physical health of the patient that their occurrence limits the ability to treat the patient with the desired amount of the anticancer therapy and/or the willingness of the patient to undertake the anticancer therapy. Protective and adjunctive agents (as discussed in paragraph [0038] below) and antiemetics can be used to ameliorate some of the side effects of some anticancer therapies; however, in many instances, anticancer therapy is administered not at the amount that would be maximally effective against the cancer cells themselves, but in an amount at which the side effects of the therapy are tolerable or treatable, the maximum tolerated dose.

Discussions of anticancer chemotherapy and biologic therapy, and their side effects, and examples of suitable therapeutic protocols, may be found in such books as *Cancer Chemotherapy and Biotherapy: Principles and Practice,* 3rd ed. (2001), Chabner and Longo, eds., and *Handbook of Cancer Chemotherapy,* 6th ed. (2003), Skeel, ed., both from Lippincott Williams & Wilkins, Philadelphia, Pa., U.S.A.; and regimens for anticancer therapies, especially chemotherapies, may be found on Web sites such as those maintained by the National Cancer Institute (www.cancer.gov), the American Society for Clinical Oncology (www.asco.org), and the National Comprehensive Cancer Network (www.nccn.org).

Glutathione (GSH), in its reduced form, is a tripeptide of the formula: γ-L-Glu-L-Cys-Gly (SEQ ID No 1). Reduced glutathione has a central role in maintaining the redox condition in cells and is also an essential substrate for glutathione S-transferase (GST). GST exists in mammals as a superfamily of isoenzymes which regulate the metabolism and detoxification of foreign substances introduced into cells. In general, GST can facilitate detoxification of foreign substances (including anticancer drugs), but it can also convert certain precursors into toxic substances. The isoenzyme GST P1-1 is constitutively expressed in many cancer cells, such as ovarian, non-small cell lung, breast, colorectal, pancreatic, and lymphoma tissue (more than 75% of human tumor specimens from breast, lung, liver, and colorectal cancers are reported to express GST P1-1). It is frequently overexpressed in tumors following treatment with many chemotherapeutic agents, and is seen in cancer cells that have developed resistance to these agents.

U.S. Pat. No. 5,556,942 discloses compounds of the formula

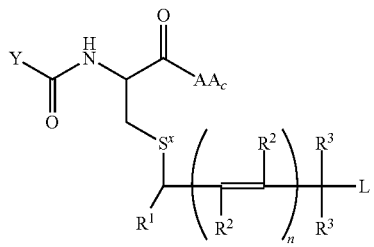

and their amides, esters, and salts, where:
L is an electron withdrawing leaving group;
$S^x$ is —S(═O)—, —S(═O)$_2$—, —S(═NH)—, —S(═O)(═NH)—, —S$^{30}$ ($C_1$-$C_6$alkyl)-, —Se(═O)—, —Se(═O)$_2$—, —Se(═NH)—, or —Se(═O)(═NH)—, or is —O—C(═O)—, or —HN—C(═O)—;
each $R^1$, $R^2$ and $R^3$ is independently H or a non-interfering substituent;
n is 0, 1 or 2;
Y is selected from the group consisting of

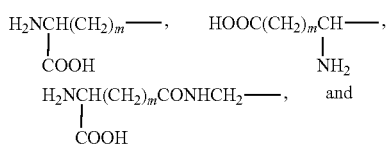

-continued
HOOC(CH$_2$)$_m$CHCONHCH$_2$—
|
NH$_2$ where m is 1 or 2; and
AA$_c$ is an amino acid linked through a peptide bond to the remainder of the compound, and their syntheses.

The compounds of the patent are stated to be useful drugs for the selective treatment of target tissues which contain compatible GST isoenzymes, and simultaneously elevate the levels of GM progenitor cells in bone marrow. Disclosed embodiments for L include those that generate a drug that is cytotoxic to unwanted cells, including the phosphoramidate and phosphorodiamidate mustards.

One of the compounds identified in the patent has the formula

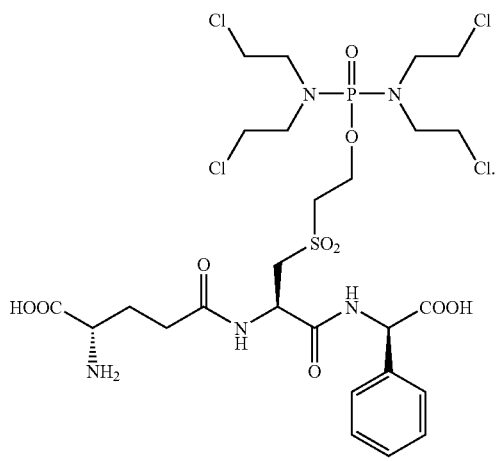

It is referred to in the patent as TER 286 and named as γ-glutamyl-α-amino-β-((2-ethyl-N,N,N,N-tetra(2'-chloro) ethylphosphoramidate) sulfonyl)propionyl-(R)-(−)phenylglycine. This compound, later referred to as TLK(286, has the CAS name L-γ-glutamyl-3-[[2-[[bis[bis(2-choroethyl)-amino]phosphinyl]oxy]ethyl]sulfonyl]-L-alanyl-2-phenyl-(2R)-glycine. As the neutral compound, its recommended International Nonproprietary Name is canfosfamide; and as its hydrochloride acid addition salt, its United States Adopted Name is canfosfamide hydrochloride. Canfosfamide and its salts are anticancer compounds that are activated by the actions of GST P1-1, and by GST A1-1, to release the cytotoxic phosphorodiamidate mustard moiety.

In vitro, canfosfamide has been shown to be more potent in the M6709 human colon carcinoma cell line selected for resistance to doxorubicin and the MCF-7 human breast carcinoma cell line selected for resistance to cyclophosphamide, both of which overexpress GST P1-1, over their parental cell lines; and in murine xenografts of M7609 engineered to have high, medium, and low levels of GST P1-1, the potency of canfosfamide hydrochloride was positively correlated with the level of GST P1-1 (Morgan et al., *Cancer Res.,* 58:2568 (1998)).

Canfosfamide, as its hydrochloride salt, is currently being evaluated in multiple clinical trials for the treatment of ovarian, breast, non-small cell lung, and colorectal cancers. It has demonstrated significant single agent antitumor activity and improvement in survival in patients with non-small cell lung cancer and ovarian cancer, and single agent antitumor activity in colorectal and breast cancer. Evidence from in vitro cell culture and tumor biopsies indicates that canfosfamide is non-cross-resistant to platinum, paclitaxel, and doxorubicin (Rosario et al., *Mol. Pharmacol.,* 58:167 (2000)), and also to gemcitabine. Patients treated with canfosfamide hydrochloride show a very low incidence of clinically significant hematological toxicity.

Other compounds specifically mentioned within U.S. Pat. No. 5,556,942 are TLK231 (TER 231), L-γ-glutamyl-3-[[2-[[bis[bis(2-chloroethyl)amino]phosphinyl]oxy]ethyl]sulfonyl]-L-alanyl-glycine, activated by GST M1a-1a; TLK(303 (TER 303), L-γ-glutamyl-3-[[2-[[bis[bis(2-chloroethyl)amino]phosphinyl]oxy]ethyl]sulfonyl]-L-alanyl-2-phenyl-(2S)-alanine, activated by GST A1-1; TLK(296 (TER 296), L-γ-glutamyl-3-[[2-[[bis[bis(2-chloroethyl)amino]phosphinyl]oxy]ethyl]sulfonyl]-L-phenylalanyl-glycine, activated by GST P1-1; and TLK297 (TER 297), L-γ-glutamyl-3-[[2-[[bis[bis(2-chloroethyl)amino]phosphinyl]oxy]ethyl]sulfonyl]-L-phenylalanyl-2-phenyl-(2R)-glycine, and their salts.

The disclosure of U.S. Pat. No. 5,556,942, and the disclosures of other documents referred to in this application, are incorporated into this application by reference.

Anticancer therapies are steadily evolving, but it remains true that even the best current therapies are not always even initially effective and frequently become ineffective after treatment, and are frequently accompanied by significant side effects, so that improved anticancer therapies are constantly being sought.

SUMMARY OF THE INVENTION

In a first aspect, this invention is a method of sensitizing a mammal, especially a human, to another anticancer therapy, that is, an anticancer therapy that is not a treatment with a GST-activated anticancer compound (including chemotherapy; molecular targeted therapy; biologic therapy; and radiotherapy, used as monotherapy or in combination), comprising administering a sensitizing effective amount of a GST-activated anticancer compound to the mammal.

In a second aspect, this invention is a pharmaceutical composition for sensitizing a mammal, especially a human, to another anticancer therapy, comprising a GST-activated anticancer compound and optionally an excipient.

In a third aspect, this invention is a method of ameliorating a side effect of another anticancer therapy in a mammal, especially a human, comprising administering an ameliorating effective amount of a GST-activated anticancer compound to the mammal.

In a fourth aspect, this invention is a pharmaceutical composition for ameliorating a side effect of another anticancer therapy in a mammal, especially a human, comprising a GST-activated anticancer compound and optionally an excipient.

In preferred embodiments of this invention (preferred embodiments of the methods, compositions, and uses of this invention as mentioned in paragraphs [0017] through [0020] above), the GST-activated anticancer compound is a compound that is an inhibitor, especially an irreversible inhibitor, of one or more GST isoenzymes and/or is a compound of U.S. Pat. No. 5,556,942, especially canfosfamide or an amide, ester, amide/ester, or salt thereof, particularly canfosfamide or a salt thereof, especially canfosfamide hydrochloride; and these preferences and preferred another anticancer therapies for which the sensitization by the GST-activated anticancer compound may be used are characterized by the specification and by the features of method claims 1 through 36 of this application as filed.

In a particular embodiment of the invention, the sensitization therapy of this invention excludes sensitization to oxaliplatin by canfosfamide and its salts, especially canfosfamide hydrochloride, and/or excludes sensitization to paclitaxel or sensitization to taxanes by canfosfamide and its salts, especially canfosfamide hydrochloride, and/or excludes sensitization by canfosfamide and its salts, especially canfosfamide hydrochloride, at a dose of 500 mg/m² or more.

In another particular embodiment of this invention, the amelioration therapy excludes amelioration of a side effect of another anticancer therapy by canfosfamide and its salts, especially canfosfamide hydrochloride, at a dose of 500 mg/m² or more.

DETAILED DESCRIPTION OF THE INVENTION

The GST-Activated Anticancer Compound

A "GST-activated anticancer compound" is a compound comprising glutathione or a glutathione analog chemically linked to a cytotoxic moiety such that the cytotoxic moiety is released by cleavage from the glutathione or glutathione analog in the presence of one or more GST isoenzymes.

Suitable such compounds include those disclosed in U.S. Pat. No. 5,556,942 and are of the formula

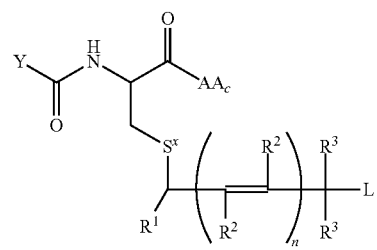

and their amides, esters, and salts, where:

L is a cytotoxic electron withdrawing leaving group;

$S^x$ is —S(=O)—, —S(=O)$_2$—, —S(=NH)—, —S(=O)(=NH)—, —S$^+$(C$_1$-C$_6$ alkyl)-, —Se(=O)—, —Se(=O)$_2$—, —Se(=NH)—, or —Se(=O)(=NH)—, or is —O—C(=O)—, or —HN—C(=O)—;

each of $R^1$, $R^2$ and $R^3$ is independently H or a non-interfering substituent, such as H, optionally substituted C$_1$-C$_6$ alkyl (for example, methyl, tert-butyl, cyclohexyl, and the like), optionally substituted C$_6$-C$_{12}$ aryl (for example, phenyl, naphthyl, pyridyl, and the like), optionally substituted C$_7$-C$_{12}$ aralkyl (for example, benzyl, phenylethyl, 2-pyridylethyl, and the like), cyano, halo, optionally substituted C$_1$-C$_6$ alkoxy, optionally substituted C$_6$-C$_{12}$ aryloxy, or optionally substituted C$_7$-C$_{12}$ aralkoxy, where the substituents may be halo, —OR, —SR, or —NR$_2$, where R is H or C$_1$-C$_4$ alkyl;

n is 0, 1 or 2;

Y is selected from the group consisting of

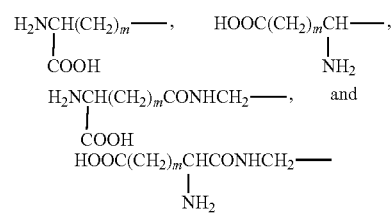

where m is 1 or 2; and

AA$_c$ is an amino acid linked through a peptide bond to the remainder of the compound.

In preferred embodiments, one or more of the following preferences is met:

L is a toxin such as ricin or diphtheria toxin, a linkable anticancer agent such as doxorubicin or daunorubicin, or a phosphoramidate or phosphorodiamidate mustard, especially a phosphorodiamidate mustard of the formula —OP(=O)(NHCH$_2$CH$_2$X)$_2$ or —OP(=O)(N(CH$_2$CH$_2$X)$_2$, particularly of the formula —OP(=O)(N(CH$_2$CH$_2$X)$_2$, where X is Cl or Br, especially Cl;

$S^x$ X is —S(=O)$_2$—;

$R^1$ is H, $C_1$-$C_4$ alkyl, or phenyl, especially H or phenyl, particularly H;

each $R^2$ is independently chosen from H and $C_1$-$C_6$ alkyl, especially H;

each $R^3$ is independently chosen from H, $C_1$-$C_4$ alkyl, and phenyl, especially H;

n is 0;

Y—C(=O)— is γ-glutamyl;

$AA_c$ is glycine, phenylglycine, β-alanine, alanine, phenylalanine, valine, 4-aminobutyric acid, aspartic acid, histidine, tryptophan, and tyrosine, as either the (S)- or (R)-isomers, optionally substituted on the phenyl ring as described above for $R^1$ through $R^3$, especially glycine, phenylglycine, β-alanine, alanine, or phenylalanine, and particularly (R)-phenylglycine.

Suitable amides and esters of these compounds include those in which one or more of the carboxyl groups is amidated or esterified to form a $C_1$-$C_6$ alkyl or alkenyl, $C_6$-$C_{10}$aryl, or $C_7$-$C_{12}$ aralkyl amide or ester, in which the alkyl or aryl groups may be optionally substituted with noninterfering substituents such as halo, alkoxy, or alkylamino. The amides and esters may be monoamides or diamides, monoesters or diesters, or monoamide-monoesters. Suitable salts (see Berge et al., *J. Pharm. Sci.*, 66:1 (1971) for a nonexclusive list) are those formed when inorganic bases (e.g. sodium, potassium, and calcium hydroxide) or organic bases (e.g. ethanolamine, diethanolamine, triethanolamine, ethylenediamine, tromethamine, N-methylglucamine) react with the carboxyl groups, and those formed when inorganic acids (e.g hydrochloric, hydrobromic, sulfuric, nitric, and chlorosulfonic acids) or organic acids (e.g. acetic, propionic, oxalic, malic, maleic, malonic, fumaric, or tartaric acids, and alkane- or arenesulfonic acids such as methanesulfonic, ethanesulfonic, benzenesulfonic, substituted benzenesulfonic such as chlorobenzenesulfonic and toluenesulfonic, naphthalenesulfonic and substituted naphthalenesulfonic, naphthalenedisulfonic and substituted naphthalenedisulfonic, and camphorsulfonic acids) react to form acid addition salts of the amine groups. Monoamide-monoester salts and ester salts are also included, as are hydrates and other solvates as well as unsolvated forms.

The preparation of these compounds and their derivatives may be made by methods well known to the person of ordinary skill in the art and as described in U.S. Pat. No. 5,556,942.

A particularly preferred GST-activated anticancer compound is canfosfamide or its salts, especially canfosfamide hydrochloride.

As a monotherapy for a number of cancers, including ovarian, breast, non-small cell lung, and colorectal cancers, canfosfamide hydrochloride has been administered by intravenous infusion at doses of 400-1000 mg/m$^2$ body surface area at once/week and once/three weeks.

As a combination therapy with cisplatin (75 and 100 mg/m), canfosfamide hydrochloride has been administered at 750 and 1000 mg/m$^2$ at 3-weekly intervals. As a combination therapy with carboplatin (AUC 5 or 6 mg/mL·min), canfosfamide hydrochloride has been administered at 500, 750, and 960 mg/m$^2$ at 3- to 4-weekly intervals. As a combination therapy with docetaxel (75 mg/m$^2$), canfosfamide hydrochloride has been administered at 500, 750, and 960 mg/m$^2$ at 3-weekly intervals. As a combination therapy with liposomal doxorubicin (40 or 50 mg/m$^2$), canfosfamide hydrochloride has been administered at 500, 750, and 960 mg/m$^2$ at 4-weekly intervals. As a combination therapy with paclitaxel (200 mg/m$^2$) and carboplatin (AUC 6 mg/mL·min), canfosfamide hydrochloride has been administered at 400, 500, 750, and 1000 mg/m$^2$ at 3-weekly intervals.

Another Anticancer Therapy

"Another anticancer therapy" is an anticancer therapy that is not a treatment with a GST-activated anticancer compound, especially an anticancer therapy that is not a treatment with a compound disclosed in paragraphs [0025] to [0030] above. Such "another anticancer therapies" include chemotherapy, molecular targeted therapy, biologic therapy, and radiotherapy. These therapies are those used as monotherapy or in combination therapy.

Chemotherapeutic agents include:

alkylating agents, including:
alkyl sulfonates such as busulfan,
ethyleneimine derivatives such as thiotepa,
nitrogen mustards such as chlorambucil, cyclophosphamide, estramustine, ifosfamide, mechlorethamine, melphalan, and uramustine,
nitrosoureas such as carmustine, lomustine, and streptozocin,
triazenes such as dacarbazine, procarbazine, and temozolamide, and
platinum compounds such as cisplatin, carboplatin, oxaliplatin, satraplatin, and picoplatin;

antimetabolites, including:
antifolates such as methotrexate, permetrexed, raltitrexed, and trimetrexate, purine analogs such as cladribine, chlorodeoxyadenosine, clofarabine, fludarabine, mercaptopurine, pentostatin, and thioguanine,
pyrimidine analogs such as azacitidine, capecitabine, cytarabine, edatrexate, floxuridine, fluorouracil, gemcitabine, and troxacitabine;

natural products, including:
antitumor antibiotics such as bleomycin, dactinomycin, mithramycin, mitomycin, mitoxantrone, porfiromycin, and anthracyclines such as daunorubicin (including liposomal daunorubicin), doxorubicin (including liposomal doxorubicin), epirubicin, idarubicin, and valrubicin,
enzymes such as L-asparaginase and PEG-L-asparaginase,
microtubule polymer stabilizers such as the taxanes paclitaxel and docetaxel,
mitotic inhibitors such as the vinca alkaloids vinblastine, vincristine, vindesine, and vinorelbine,
topoisomerase I inhibitors such as the camptothecins irinotecan and topotecan, and
topoisomerase II inhibitors such as amsacrine, etoposide, and teniposide;

hormones and hormone antagonists, including:
androgens such as fluoxymesterone and testolactone,
antiandrogens such as bicalutamide, cyproterone, flutamide, and nilutamide,
aromatase inhibitors such as aminoglutethimide, anastrozole, exemestane, formestane, and letrozole,
corticosteroids such as dexamethasone and prednisone,
estrogens such as diethylstilbestrol,
antiestrogens such as fulvestrant, raloxifene, tamoxifen, and toremifine,
LHRH agonists and antagonists such as buserelin, goserelin, leuprolide, and triptorelin, progestins such as medroxyprogesterone acetate and megestrol acetate, and
thyroid hormones such as levothyroxine and liothyronine; and
miscellaneous agents, including altretamine, arsenic trioxide, gallium nitrate, hydroxyurea, levamisole,
mitotane, octreotide, procarbazine, suramin, thalidomide, lenalidomide, photodynamic compounds such as methoxsalen and sodium porfimer, and proteasome inhibitors such as bortezomib.

Molecular targeted therapy agents include:
functional therapeutic agents, including:
gene therapy agents,
antisense therapy agents,
tyrosine kinase inhibitors such as erlotinib hydrochloride, gefitinib, imatinib mesylate, and semaxanib, and
gene expression modulators such as the retinoids and rexinoids, e.g. adapalene, bexarotene, trans-retinoic acid, 9-cis-retinoic acid, and N-(4-hydroxyphenyl)retinamide;
phenotype-directed therapy agents, including:
monoclonal antibodies such as alemtuzumab, bevacizumab, cetuximab, ibritumomab tiuxetan, rituximab, and trastuzumab,
immunotoxins such as gemtuzumab ozogamicin,
radioimmunoconjugates such as $^{131}$I-tositumomab, and
cancer vaccines.

Biologic therapy agents include:
interferons such as interferon-$\alpha_{2a}$ and interferon-$\alpha_{2b}$, and
interleukins such as aldesleukin, denileukin diftitox, and oprelvekin.

In addition to these agents intended to act against cancer cells, anticancer therapies include the use of protective or adjunctive agents, including:
cytoprotective agents such as amifostine, dexrazoxane, and mesna,
phosphonates such as pamidronate and zoledronic acid, and
stimulating factors such as epoetin, darbeopetin, filgrastim, PEG-filgrastim, and sargramostim.

Combination anticancer therapy regimens to which the GST-activated anticancer compound may be used to sensitize a mammal to and/or for which the GST-activated anticancer compound can be used to ameliorate a side effect of that therapy include all regimens involving the use of two or more of the anticancer therapies (anticancer agents) such as those mentioned in paragraphs [0034] to [0037] above and/or radiotherapy, optionally including protective and adjunctive agents such as those mentioned in paragraph [0038] above; and the GST-activated anticancer compound can be used to sensitize a mammal to and/or ameliorate a side effect of existing anticancer regimens known for the treatment of various cancers, such as the regimens mentioned in paragraph [0007] above.

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, methotrexate-leucovorin, and those known by the acronyms ABDIC, ABVD, AC, ADIC, AI, BACOD, BACOP, BVCPP, CABO, CAD, CAE, CAL, CAP, CD, CEC, CL, CHOP, CHOP+rituximab, CIC, CMF, CMLP, CyADIC, CyVADIC, DAC, DVD, FAC, FAC-S, FAM-S, FOLLOX-4, FOLLOX-6, M-BACOD, MACOB-B, MAID, MOPP, MVAC, PCV, T-5, VAC, VAD, VAPA, VAP-Cyclo, VAP-II, VBM, VBMCP, VIP, VP, and the like.

Combinations of chemotherapies and molecular targeted therapies, biologic therapies, and radiation therapies are also well known to the art; including therapies such as trastuzumab+paclitaxel, alone or in further combination with carboplatin, for certain breast cancers, and many other such regimens for other cancers; and the "Dublin regimen" (555 mg/m$^2$ fluorouracil IV over 16 hours on days 1-5 and 75 mg/m$^2$ cisplatin IV over 8 hours on day 7, with repetition at 6 weeks, in combination with 40 Gy radiotherapy in 15 fractions over the first 3 weeks) and the "Michigan regimen" (fluorouracil+cisplatin+vinblastine+radiotherapy), both for esophageal cancer, and many other such regimens for other cancers.

Sensitization to Another Anticancer Therapy and/or Amelioration of a Side Effect of Another Anticancer Therapy by Treatment with a GST-Activated Anticancer Compound This invention is a method of sensitizing a mammal, especially a human, to another anticancer therapy, comprising administering a sensitizing effective amount of a GST-activated anticancer compound to the mammal; and is also a method of ameliorating a side effect of another anticancer therapy in a mammal, especially a human, comprising administering an ameliorating effective amount of a GST-activated anticancer compound to the mammal.

A "sensitizing effective amount" of the GST-activated anticancer compound means that amount which, when administered to a mammal, especially a human, for treating a cancer with another anticancer therapy, is sufficient to sensitize the mammal to the another anticancer therapy. "Sensitizing" or "sensitization" of a mammal to another anticancer therapy includes one or both of:
(1) increasing the efficacy of the another anticancer therapy in a mammal naïve to that therapy ("initial sensitization"), and
(2) increasing the efficacy of the another anticancer therapy in a mammal that has already received that therapy, in particular in a mammal that has received that therapy and been refractory or become resistant to it ("resensitization").

In the case of initial sensitization, increasing the efficacy of the another anticancer therapy includes causing the therapeutically effective amount of that another anticancer therapy to be lower than it would be if the initial sensitization had not occurred (so that a lesser dose and/or reduced frequency of dosing can be used to achieve the same anticancer effect, thereby achieving equally effective therapy with that another anticancer therapy with no or fewer side effects), causing the amount of the another anticancer therapy that is therapeutically effective if the initial sensitization had not occurred to be more effective (so that a greater anticancer effect is achieved at the same amount of the another anticancer therapy), and/or inhibiting the development of resistance to the another anticancer therapy (preventing, delaying the onset of, and/or limiting the extent of resistance to that therapy). In the case of resensitization, increasing the efficacy of the another anticancer therapy includes these same effects described for initial sensitization, and particularly includes enabling the therapeutically effective reuse of another anticancer therapy to which resistance has developed (enabling the re-treating of a cancer with another anticancer therapy that, prior to the resensitization, had become resistant or refractory to that therapy).

An "ameliorating effective amount" of the GST-activated anticancer compound means that amount which, when administered to a mammal, especially a human, being treated for a cancer with another anticancer therapy, is sufficient to ameliorate one or more of the side effects of the another anticancer therapy. "Ameliorating" or "amelioration" of a side effect of another anticancer therapy includes one or more of:
(1) preventing the occurrence of that side effect; and
(2) limiting the severity of that side effect.

The side effects that may be ameliorated by treatment with the GST-activated anticancer compound may include any one or more of the known side effects of the another anticancer therapy. Such side effects include alopecia, nausea and/or vomiting, hematologic side effects such as neutropenia, neurologic side effects such as peripheral neuropathy, and the like.

A "therapeutically effective amount" of the another anticancer therapy means that amount which, when administered to a mammal, especially a human, for treating a cancer, is sufficient to effect treatment for the cancer. "Treating" or "treatment" of a cancer in a mammal includes one or more of:
(1) inhibiting growth of the cancer, i.e., arresting its development,
(2) preventing spread of the cancer, i.e. preventing metastases,
(3) relieving the cancer, i.e., causing regression of the cancer,
(4) preventing recurrence of the cancer, and
(5) palliating symptoms of the cancer.

Cancers which may be effectively treated by the method of this invention include mammalian cancers, especially human cancers. Cancers that are particularly treatable by the method of this invention are cancers with sensitivity to inducers of apoptosis, and more specifically those cancers that express or, particularly, overexpress one or more glutathione S-transferase isoenzymes. Cancers that express or overexpress one or more glutathione S-transferase isoenzymes when treated with other anticancer compounds or combination anticancer chemotherapy regimens (i.e. those not including a GST-activated anticancer compound) are especially treatable by the method of this invention. Such cancers include cancers of the brain, breast, bladder, cervix, colon and rectum, esophagus, head and neck, kidney, lung, liver, ovary, pancreas, prostate, and stomach; leukemias such as ALL, AML, AMML, CLL, CML, CMML, and hairy cell leukemia; Hodgkin's and non-Hodgkin's lymphomas; mesotheliomas, multiple myeloma; and sarcomas of bone and soft tissue. Cancers particularly treatable by the method of this invention with canfosfamide and its salts as the GST-activated anticancer compound include breast, ovarian, colorectal, and non-small cell lung cancers; and TLK296 would also be useful for the same cancers because it also is activated by GST P1-1. Other GST-activated anticancer compounds are expected to be suitable for these or other cancers depending on the nature of the GST isoenzymes expressed by the cancer being treated.

Another anticancer therapies which may particularly benefit from the sensitization and/or amelioration method of this invention are those therapies where one or more GST isoenzymes are implicated in the action of that anticancer therapy; and particularly therapies involving the administration of platinum compounds such as cisplatin, carboplatin, oxaliplatin, satraplatin, and picoplatin, especially cisplatin and carboplatin; taxanes, such as paclitaxel and docetaxel; and anthracyclines such as daunorubicin, doxorubicin, epirubicin, idarubicin, and valrubicin. Thus the method of this invention particularly includes the sensitization to anticancer therapies involving platinum compounds, taxanes, and anthracyclines by administering a GST-activated anticancer compound of this invention; and the amelioration of a side effect, such as alopecia, of anticancer therapies involving platinum compounds, taxanes, and anthracyclines by a GST-activated anticancer compound of this invention.

The method of this invention therefore also comprises the administration of a sensitizing and/or ameliorating effective amount of a GST-activated anticancer compound and a therapeutically active amount of another anticancer therapy. The another anticancer therapy will generally be one that has utility in the treatment of the cancer being treated even without the sensitization and/or amelioration effect of the GST-activated anticancer compound; and a suitable such another anticancer therapy for a particular cancer to be treated will be determinable by a person of ordinary skill in the art having regard to that knowledge and this disclosure. It is of course contemplated that the sensitization and/or amelioration therapy of this invention may be used with anticancer therapies not yet in use. The GST-activated anticancer agent may also be used as adjuvant or neoadjuvant therapy accompanying radiation therapy.

For sensitization, the amount of the GST-activated anticancer compound that is administered to the mammal should be a sensitizing effective amount for the another anticancer therapy; and similarly the amount of the another anticancer therapy that is administered to the mammal should be a therapeutically effective amount when the mammal has been sensitized with the GST-activated anticancer compound. However, the sensitizing effective amount of the GST-activated anticancer compound may be different depending on the another anticancer therapy; and the therapeutically effective amount of the another anticancer therapy when administered in the method of this invention may be less than the amount which would be therapeutically effective if delivered to the mammal without sensitization. It is common in cancer therapy, though, to use the maximum tolerated dose of the or each therapy, with a reduction only because of common toxicity of the therapies used or potentiation of the toxicity of one therapy by another. Because of the lack of cross-resistance of canfosfamide and its salts, especially canfosfamide hydrochloride, for example, with several common chemotherapeutic agents, and its relative lack of clinically severe toxicity, especially its lack of clinically severe hematological toxicity, it is expected that no reduction in the amount of the another anticancer therapy will be required.

For amelioration, the amount of the GST-activated anticancer compound that is administered to the mammal should be an ameliorating effective amount for the another anticancer therapy; and similarly the amount of the another anticancer therapy that is administered to the mammal should be a therapeutically effective amount when a side effect has been ameliorated with the GST-activated anticancer compound. However, the ameliorating effective amount of the GST-activated anticancer compound may be different depending on the another anticancer therapy; and the therapeutically effective amount of the another anticancer therapy when administered in the method of this invention may be less than the amount which would be therapeutically effective if delivered to the mammal without amelioration (since the GST-activated anticancer compound may also sensitize the mammal to that another anticancer therapy, as discussed elsewhere in this application). It is common in cancer therapy, though, to use the maximum tolerated dose of the or each therapy, with a reduction only because of common toxicity of the therapies used or potentiation of the toxicity of one therapy by another. Because of the lack of cross-resistance of canfosfamide and its salts, especially canfosfamide hydrochloride, for example, with several common chemotherapeutic agents, and its relative lack of clinically severe toxicity, especially its lack of clinically severe hematological toxicity, it is expected that no reduction in the amount of the another anticancer therapy will be required; and the amount of the another anticancer therapy that may be able to be administered may be higher than the usual dosage because of the amelioration of a side effect of that another anticancer therapy provided by the GST-activated anticancer compound.

The sensitization and/or amelioration therapy may involve the administration of the GST-activated anticancer compound before or during the administration of the another anticancer therapy. The administration of the GST-activated anticancer compound may precede at least one aspect of the another anticancer therapy (such as the administration of one dose of a chemotherapeutic agent, molecular targeted therapy agent, biologic therapy agent, or radiation therapy) by as little as a few minutes (for example, during the same day, e.g. during the same treatment visit) to as much as several weeks, for example from one to five weeks, e.g. one to three weeks.

Although not wishing to be bound by theory, it is considered that sensitization and/or amelioration therapy with the GST-activated anticancer compound, particularly a GST P1-1 activated anticancer compound such as canfosfamide and its salts, especially canfosfamide hydrochloride, and another anticancer therapy will be of benefit because of one or both of the following mechanisms:

(1) GST P1-1 is overexpressed in many cancer cell lines, and particularly in cell lines treated with known anticancer therapies such as treatment with platinum-containing compounds and doxorubicin; and the increase in GST P1-1 is correlated with an increase in resistance to the anticancer therapy. Because compounds such as canfosfamide are activated by GST P1-1, cancer cells that have been treated with another anticancer therapy will contain an elevated level of GST P1-1 and will therefore increase the activity of canfosfamide in these cells. Thus a GST-activated anticancer compound such as canfosfamide or its salt will be especially potent in resensitization and in sensitization in cancer cells that already overexpress GST P1-1. Likewise other GST-activated anticancer compounds activated by other GST isoenzymes may be especially effective as sensitizers in cancers in which those other GST isoenzymes are implicated; and (2) Compounds such as canfosfamide are activated by GST P1-1, and this activation is achieved by interaction of the canfosfamide with the active site of the enzyme. This interaction will limit the ability of the enzyme to interact with and detoxify other anticancer agents which might otherwise be detoxified by GST P1-1, thereby effectively increasing the cytotoxicity of (reducing the therapeutically effective amount of these other anticancer agents. Thus administration of a GST-activated anticancer compound such as canfosfamide or its salt as a sensitizing agent will make the another anticancer therapy more effective than it would have been without the sensitization, and may re-enable use of another anticancer therapy to which the cancer has become resistant or refractory. In particular, because certain of these GST-activated anticancer compounds, such as canfosfamide, are irreversible inhibitors of GST P1-1, they may be especially effective in the sensitization method of this invention. Likewise, other GST-activated anticancer compounds interacting with and/or inhibiting other GST isoenzymes may be especially effective as sensitizers in cancers in which those other GST isoenzymes are implicated. Insofar as the toxicities (side effects) of any of the another anticancer therapies may be influenced by the interaction of the another anticancer therapies with a GST isoenzyme (such as GST P1-1), inhibition of the GST isoenzymes may also ameliorate a side effect of that another anticancer therapy, and thus GST-activated anticancer compounds like canfosfamide and its salts may be especially effective as ameliorators of the side effects of these anticancer therapies.

Suitable sensitization and/or amelioration dosing for canfosfamide or its salt as the GST-activated anticancer compound may be the same as the usual therapeutic dose, but will preferably be below the usual therapeutic dose, such as about 5-75% of the usual therapeutic dose, e.g. about 10-50% of the usual therapeutic dose, such as 20%, 25%, or 30% of the usual therapeutic dose; for example about 60-450 mg/m$^2$ body surface area, especially 125-450 mg/m$^2$ for canfosfamide hydrochloride. Dosing may be at 1-35 day intervals; for example, about 125-450 mg/m$^2$ at 1-5 week intervals, especially at 1, 2, 3, or 4 week intervals, or at higher frequencies including as frequently as once/day for several (e.g. 5 or 7) days, with the dosing repeated every 2, 3, or 4 weeks, or constant infusion for a period of 6-72 hours, also with the dosing repeated every 2, 3, or 4 weeks; and such dosing flexibility will readily enable sensitization and/or amelioration for the anticancer therapies now used. Suitable dosages and dose frequencies for other GST-activated anticancer compounds will also preferably be below the usual therapeutic dose, such as about 5-50% of the usual therapeutic dose, e.g. 10-50% of the usual therapeutic dose, and will be readily determinable by a person of ordinary skill in the art having regard to that skill and this disclosure.

Suitable dosing for the other anticancer therapy will be the dosing already established for that therapy, as described in documents such as those cited in paragraph [0007], recognizing that the therapeutically effective amount of the another anticancer therapy may be reduced by the sensitization of this invention. Such dosing varies widely with the therapy: for example, capecitabine (2500 mg/m$^2$ orally) is dosed twice daily for 2 weeks on and 1 week off, imatinib mesylate (400 or 600 mg/day orally) is dosed daily, rituximab is dosed weekly, paclitaxel (135-175 mg/m$^2$) and docetaxel (60-100 mg/m$^2$) are dosed weekly to every three weeks, carboplatin (4-6 mg/mL·min) is dosed once every 3 or 4 weeks (though the doses may be split and administered over several days), nitrosourea alkylating agents such as carmustine are dosed as infrequently as once every 6 weeks. Radiotherapy may be administered as frequently as weekly (or even within that split into smaller dosages administered daily).

A person of ordinary skill in the art of anticancer therapy will be able to ascertain a sensitizing and/or ameliorating effective amount of the GST-activated anticancer compound and a therapeutically effective amount of another anticancer therapy for a given cancer and stage of disease without undue experimentation and in reliance upon personal knowledge and the disclosure of this application.

The GST-activated anticancer compound and the another anticancer therapy may be administered by any route suitable to the subject being treated and the nature of the subject's condition. Routes of administration include, but are not limited to, administration by injection, including intravenous, intraperitoneal, intramuscular, and subcutaneous injection, by transmucosal or transdermal delivery, through topical applications, nasal spray, suppository and the like or may be administered orally. Formulations may optionally be liposomal formulations, emulsions, formulations designed to administer the drug across mucosal membranes or transdermal formulations. Suitable formulations for each of these methods of administration may be found, for example, in *Remington: The Science and Practice of Pharmacy,* 20th ed., A. Gennaro, ed., Lippincott Williams & Wilkins, Philadelphia, Pa., U.S.A. Typical formulations will be either oral (as for compounds such as capecitabine) or solutions for intravenous infusion. Typical dosage forms will be tablets (for oral administration), solutions for intravenous infusion, and lyophilized powders for reconstitution as solutions for intravenous infusion. Although anticancer therapies are usually administered systemically, it is contemplated that the GST-activated anticancer compound may also be administered regionally, such as peritumorally or intratumorally, to sensitize the cancer to the another anticancer therapy administered either systemically or regionally.

Another anticancer therapies considered of particular present interest for sensitization or side effect amelioration by the method of this invention, especially with canfosfamide or its salt, include: a platinum compound such as carboplatin or cisplatin, optionally in combination with gemcitabine or a taxane such as docetaxel or paclitaxel; with gemcitabine; a taxane; an anthracycline such as doxorubicin or liposomal doxorubicin; oxaliplatin, optionally in combination with capecitabine or fluorouracil/leucovorin; and gemcitabine or a platinum compound such as carboplatin or cisplatin, in combination with a vinca alkaloid such as vinorelbine. It will be seen from the in vitro example that follows that canfosfamide hydrochloride causes sensitization to paclitaxel and, as mentioned previously, it is expected that canfosfamide or its salts or other GST-activated anticancer compounds can be used to sensitize to other anticancer therapies generally; and it will be seen from the clinical observation that follows that canfosfamide hydrochloride ameliorates the alopecia side effect of carboplatin and, as mentioned previously, it is expected that canfosfamide and its salts or other GST-activated anticancer compounds can be used to ameliorate a side effect of other anticancer therapies generally.

In Vitro Example

The following example illustrates the beneficial effect of canfosfamide, a GST-activated anticancer compound, in sensitizing human cancer cell lines in vitro to the effect of another anticancer agent. This result is considered predictive of efficacy in human anticancer chemotherapy, as each of canfosfamide and the other anticancer agent tested have shown anticancer activity in humans.

Cancer cell line. The human cancer cell line OVCAR-3 (ovarian adenocarcinoma) was obtained from the National Cancer Institute, Bethesda, Md., U.S.A.

Anticancer compounds. Canfosfamide was prepared for Telik. Paclitaxel was obtained from Sigma-Aldrich Chemical Company, St. Louis, Mo., U.S.A.

Example 1

Canfosfamide Hydrochloride and Paclitaxel

A paclitaxel-resistant derivative cell line OVCAR-PR was developed from the human ovarian cancer cell line OVCAR-3 by growing OVCAR-3 cells in gradually increasing concentrations (up to 5 nM) of paclitaxel. A canfosfamide-modified derivative cell line OVCAR-TLK was developed by growing OVCAR-3 cells in gradually increasing concentrations (up to 6.5 µM) of canfosfamide. To maintain the phenotypes of the cell lines, the cells were treated with the compounds at weekly intervals. Cells were grown in compound-free media for 24 hours before any experiments.

Cytotoxicity assay. Log-phase cells were seeded in 96-well plates and incubated with the diluted compound or solvent for 2-3 doubling times. The extent of cell growth was quantitated using the CellTiter-Glo assay (Promega Corporation, Madison, Wis., U.S.A.), used in accordance with the assay kit directions. The amount of ATP in the lysate, which corresponds to the number of viable cells, was quantitated using a luminometer. All assays were conducted in triplicate wells, with solvent control. The extent of cell growth was expressed as a percentage of the signal from the solvent control wells. The mean of the triplicate wells was computed and $IC_{50}$ determined using PrismGraph.

Cell doubling time. $1.5 \times 10^4$ cells were seeded in a 25-mL flask. The cells were grown for four days and the number of viable cells was determined by Trypan Blue staining and manual counting using a hemocytometer. The assay was conducted in triplicate at each time point. The times for two cell doublings for OVCAR-3 and OVCAR-TLK cells were approximately 3.5 and 5.5 days, respectively.

Results: The $IC_{50}$ for paclitaxel increased from 1.3 nM in OVCAR-3-cells to 49 nM in OVCAR-PR cells, a more than 35-fold increase in resistance. However, the $IC_{50}$ for canfosfamide increased from 1.3 µM in OVCAR-3 cells to only 1.6 µM nM in OVCAR-PR cells, only a 1.2-fold increase in resistance. When the OVCAR-PR cells were first treated overnight with 4 µM canfosfamide, then tested for their response to paclitaxel, the $IC_{50}$ for paclitaxel decreased approximately 3-fold, indicating sensitization of these formerly paclitaxel-resistant cells by treatment with canfosfamide. When OVCAR-3 and OVCAR-TLK cells were treated with paclitaxel for equal treatment times, the $IC_{50}$s for paclitaxel were approximately the same, but when the cells were treated for treatment times adjusted for the differential doubling times (treated for approximately two doubling times), the $IC_{50}$ for paclitaxel of was about 2-fold lower in the OVCAR-TLJK cells, indicating sensitization of even these non-paclitaxel-resistant cells by treatment with canfosfamide. OVCAR-3 and OVCAR-TLJK cells were approximately equally sensitive to canfosfamide when treated for approximately two doubling times.

Therapeutic Examples

Sensitization to Another Anticancer Therapies with Canfosfamide

Canfosfamide at an initial dose of 500 mg/m$^2$ is administered intravenously, followed 30 minutes later by the intravenous administration of oxaliplatin at a therapeutically effective dose such as 85 mg/m$^2$. The canfosfamide dose may be increased to 850 mg/m$^2$ and further to 1280 mg/m$^2$, and the oxaliplatin dose may also be varied. This combination is administered at 2-weekly intervals.

Canfosfamide at an initial dose of 500 mg/m$^2$ is administered intravenously at 3-weekly intervals, accompanied by the oral administration of capecitabine at a therapeutically effective dose such as 1250 mg/m$^2$ twice/day for 14 days, followed by 7 days without treatment. The canfosfamide dose may be increased to 750 mg/m$^2$ and further to 960 mg/m$^2$, and the capecitabine dose may also be varied.

Canfosfamide at an initial dose of 400 mg/m$^2$ is administered intravenously at 2-weekly intervals, followed 30 minutes later by the intravenous administration of fluorouracil at a therapeutically effective dose such as 12 mg/Kg, with leucovorin rescue after completion of four days of fluorouracil therapy. The canfosfamide dose may be increased to 700 mg/m$^2$ and further to 1000 mg/m$^2$, and the fluorouracil dose may also be varied.

Ovarian cancer patients treated with carboplatin-containing regimens underwent repeated cycles of alopecia corresponding to the administration of the carboplatin. The same patients, when treated with carboplatin at AUC 5 or 6 mg/mL·min in combination with canfosfamide hydrochloride at 500 mg/m$^2$ and carboplatin at AUC 6 mg/mL·min in combination with canfosfamide hydrochloride at 750, and 960 mg/m$^2$ did not experience the same recurrence of alopecia with treatment, illustrating the amelioration of this side effect of carboplatin therapy by treatment with canfosfamide hydrochloride. Other side effects such as the hematologic and neurologic side effects of carboplatin were similarly ameliorated.

Other GST-activated anticancer compounds may be used similarly in the methods of this invention. Different other anticancer therapies, such as other chemotherapies, molecularly targeted therapies, biologic therapies, and radiation therapies may also be used similarly in the methods of this invention and will benefit from the sensitization and/or side effect amelioration induced by treatment with the GST-activated anticancer compounds.

While this invention has been described in conjunction with specific embodiments and examples, it will be apparent to a person of ordinary skill in the art, having regard to that skill and this disclosure, that equivalents of the specifically disclosed materials and methods wilt also be applicable to this invention; and such equivalents are intended to be included within the following claims.

We claim:

1. A method of limiting the severity of a side effect of anticancer therapy in a human patient undergoing anticancer therapy and exhibiting a deleterious side effect of such therapy, wherein said anticancer therapy comprises administration of an alkylating agent selected from the group consisting of cisplatin, carboplatin, oxaliplatin, satraplatin, and picoplatin, and said method comprises:
  a) identifying the human patient undergoing anticancer therapy and exhibiting the deleterious side effect of such anticancer therapy provided that such anticancer therapy is not treatment with canfosfamide or a salt thereof; and
  b) administering a side effect limiting effective amount of a compound that is canfosfamide or a salt thereof.

2. The method of claim 1 where the compound is canfosfamide hydrochloride.

* * * * *

SEQUENCE LISTING

<160> NUMBER OF SEQ ID NOS: 1

<210> SEQ ID NO 1
<211> LENGTH: 3
<212> TYPE: PRT
<213> ORGANISM: Artificial Sequence
<220> FEATURE:
<223> OTHER INFORMATION: Glutathione
<220> FEATURE:
<221> NAME/KEY: MISC_FEATURE
<222> LOCATION: 1
<223> OTHER INFORMATION: the Glu amino acid residue is gamma L-glutamic
      acid
<220> FEATURE:
<221> NAME/KEY: MISC_FEATURE
<222> LOCATION: 2
<223> OTHER INFORMATION: the Cys amino acid residue is L-cysteine

<400> SEQUENCE: 1

Glu Cys Gly
1